United States Patent
Sferrazza

(10) Patent No.: US 9,420,796 B2
(45) Date of Patent: Aug. 23, 2016

(54) CONTROL OF ZEBRA MUSSELS IN FLOW-THROUGH SERVICE WATER SYSTEMS

(71) Applicant: ASI Group Ltd., St. Catharines (CA)

(72) Inventor: Carmelo Sferrazza, Fonthill (CA)

(73) Assignee: ASI Group Ltd., St. Catharines, ON (CA)

( * ) Notice: Subject to any disclaimer, the term of this patent is extended or adjusted under 35 U.S.C. 154(b) by 0 days.

(21) Appl. No.: 13/756,080

(22) Filed: Jan. 31, 2013

(65) Prior Publication Data

US 2014/0208634 A1    Jul. 31, 2014

(51) Int. Cl.
*A01M 25/00* (2006.01)
*A01N 59/00* (2006.01)
*C02F 1/76* (2006.01)

(52) U.S. Cl.
CPC .............. *A01N 59/00* (2013.01); *A01M 25/00* (2013.01); *C02F 1/76* (2013.01); *C02F 2303/185* (2013.01); *Y02W 10/37* (2015.05)

(58) Field of Classification Search
USPC ........... 43/124; 210/754, 755, 753, 756, 739; 119/650–651
See application file for complete search history.

(56) References Cited

U.S. PATENT DOCUMENTS 5,096,601 A * 3/1992 Muia et al. ................... 210/755
5,442,967 A * 8/1995 McClane ................... 73/863.22

FOREIGN PATENT DOCUMENTS

| CA | 2091928 | 10/1993 |
| CA | 2230582 | 3/1997 |

OTHER PUBLICATIONS

"Zebra Mussel Chemical Control Guide" Jan. 2000, by Susan L. Sprecher and Kurt D. Getsinger, US Army Corps of Engineers.*
Srung, M., "Field and laboratory observations of Dreissena polymorpha larvae: abundance, growth, mortality and food demands." Arch Hydrobiol, 1989, 115:537-561.

* cited by examiner

*Primary Examiner* — David Parsley
(74) *Attorney, Agent, or Firm* — Bereskin & Parr LLP/S.E.N.C.R.L., s.r.l.; I. Laurence MacPhie

(57) ABSTRACT

A method for controlling bivalve growth in a service water system of a plant is disclosed. Upon detecting an increase in the number of veligers or settlement stage bivalves, chlorine anion is introduced into the service water to obtain a chlorine anion concentration of between 0.10 and 2.0 mg/l for a period of 10 to 40 days. Also disclosed is a two-stage method for controlling bivalve growth in a service water system.

16 Claims, 8 Drawing Sheets

Colonized Plates: S = 0.75 - 2.0 mm Mussels

L = 2.5 - 5.0 mm Mussels

A

B

C

CONTROL OF ZEBRA MUSSELS IN FLOW-THROUGH SERVICE WATER SYSTEMS

FIELD

The invention relates to methods for controlling bivalve growth in the service water system of a plant. More specifically, the invention relates to methods for controlling bivalve growth in a flow-through service water system using chlorine anions.

BACKGROUND

The introduction of the zebra mussel (*Dreissena polymorpha*) to North America in 1986 has had a dramatic impact on water users throughout the continent. This organism has colonized the entire Great Lakes system, the Mississippi River and associated tributaries and inland waterways throughout North America. Another species of mussel, the quagga mussel (*Dreissena bugensis*) was introduced in the 1990's and has also spread throughout North America.

Although they are separate species they share a trait which has been devastating to raw water users throughout the continent. Mussel veligers (initial offspring) reach a stage in their maturation wherein they settle and attach themselves to hard surfaces. This is particularly troublesome for industrial water users as service water piping provides an ideal surface for attachment. Resulting problems include reduction of pipes bores and associated cooling capacity, enhanced electro-corrosion of steel and increased maintenance costs associated with the accumulation of shell debris. Since the early 1990's, industry has spent millions of dollars searching for mitigation methods which are reliable, cost effective and safe.

Traditionally, continuous, high-level chlorination via permanent chemical injection facilities has been the most widely implemented treatment methodology for mussel control. The process required that incoming raw water was chlorinated continuously throughout the organism's reproductive period (May-December) thereby preventing colonization. However these methods are encumbered by a number of factors including the high cost of operation of chlorination systems and increased environmental risk due to long extended periods of chemical use and storage.

Canadian Patent Application No. 2,230,582 describes a process for inhibiting the settlement of post-veliger zebra mussels which requires a chlorine dioxide generator to intermittently pump chlorine dioxide into the water system to obtain and maintain a chlorine dioxide concentration of 0.1-0.5 ppm for a period of 10 minutes to 120 minutes. The process is carried out at least 5 days per week each week during the zebra mussel spawning season, typically between April and October. Chlorine dioxide is unstable and potentially explosive and therefore requires the use of an on-site chlorine dioxide generator.

Canadian Patent Application No. 2,091,928 describes the treatment of fresh water to control and prevent infestation by zebra mussels at submerged offshore water intake facilities where water containing chlorine dioxide is continuously or intermittently injected for a treatment period of 1 to 14 days. Experiments carried out to evaluate continuous 24 hour treatment using $ClO_2$ (chlorine dioxide), NaOCl (sodium hypochlorite), KMnO, or $NaClO_2$ (sodium chlorite) were disclosed and only chlorine dioxide was reported to have achieved acceptable mortality rates of 50% at 2 ppm and 90% at 5 ppm, while the other chemicals achieved no mortality or mortality rates of only 10%.

There remains a need for new and improved methods for controlling bivalve growth in the service water systems.

SUMMARY

In one aspect there is provided a method for controlling bivalve growth in the flow-through service water system of a plant. The methods described herein present a number of advantages for controlling bivalve growth in service water systems such as reducing the time and/or the amount of chemical required for the killing or eradication of bivalves. In particular, by targeting settlement stage bivalves with chlorine anions at the beginning and/or the end of the reproductive cycle, the need for continuous treatment spanning the entire reproductive period of the bivalves (approximately 6 months) is eliminated.

In another aspect, there is provided a method of treating service water with low concentrations of chlorine anions (i.e. less than 2 mg/l, preferably less than 1 mg/l) in order to induce mortality in target bivalves. Veligers and early-stage bivalves are more sensitive than adult bivalves to chlorine anions such that relatively low concentrations can effectively be used at early stages of the reproductive period to control bivalve-growth. Optionally, the methods described herein involve two or more separate treatment periods near the beginning and the end of the target bivalves' reproductive period. In particular, by targeting the bivalves with chlorine anions near the beginning and/or end of the reproductive cycle the need for continuous treatment spanning the entire reproductive period of the bivalves (approximately 6 months) is eliminated. In one embodiment, preventing the settlement and/or translocation of veligers and/or early stage bivalves into the service water system and not merely killing adult bivalves, helps reduce the shell load within the service water system preventing the accumulation of shell debris. As shown in Example 2, it has surprisingly been determined that the settlement and translocation of veligers and early stage bivalves can be inhibited at concentrations of chlorine anions as low as 0.1 mg/l, optionally between 0.1 mg/l and 0.2 mg/l, and preferably about 0.3 mg/l or greater.

Accordingly, the methods described herein are useful for controlling bivalve growth by introducing chlorine anions into service water of a service water system for shorter periods of time without the need for continuous treatment. Furthermore, the methods can be implemented using portable systems which avoid the need for costly permanent chemical injection systems or on-site chlorine dioxide generators.

Other advantages of the methods described herein include the use of live specimen bioassays to determine the effectiveness of the treatment and prevent under or over treating the service water. The methods described herein optionally include treating the effluent of the service water system to neutralize residual chlorine thereby reducing the environmental impact.

In one aspect, there is provided a two-stage method for controlling bivalve growth in a service water system of a plant wherein service water is drawn from a body of water and generally continuously flowed through the service water system. In one embodiment, the method comprises:

a. monitoring the body of water for the presence of veligers and/or early stage bivalves;
b. when an increase in the concentration of veligers and/or early stage bivalves is detected, introducing chlorine anion into the service water of the service water system in an amount sufficient to obtain a steady state chlorine anion concentration of 0.1 to 2.0 mg/l;

c. maintaining the steady state concentration of chlorine anion in the service water of the service water system for a first treatment period of 10 to 40 days;
d. monitoring the body of water for the presence of pediveligers and/or settlement stage bivalves;
e. when an increase in the concentration of pediveligers and/or settlement stage bivalves is detected, introducing chlorine anion into the service water of the service water system in an amount sufficient to obtain a steady state chlorine anion concentration of 0.1 to 2.0 mg/l; and
f. maintaining the steady state concentration of chlorine anion in the service water of the service water system for a second treatment period of 10 to 40 days.

Optionally, the method further comprises monitoring a live colony of the bivalves in the service water of the service water system or under chlorine anion concentrations and temperatures comparable to those in the service water system and terminating the first treatment period and/or second treatment period after the bivalves in the live colony die.

In one embodiment, the first treatment period is initiated after the start of the bivalves' reproductive period and the second treatment period is initiated towards the end of the bivalves' reproductive period. In one embodiment, the first treatment period is initiated in the May, June or July and the second treatment period is initiated in August, September, October, November or December. In one embodiment, the first treatment period is initiated 4 to 6 weeks after the increase in the concentration of veligers and/or early stage bivalves is detected. In one embodiment, the second treatment period is initiated 8 to 24 weeks after the first treatment period is terminated.

In one aspect, there is provided a method for controlling bivalve growth in a service water system of a plant wherein service water is drawn from a body of water and generally continuously flowed through the service water system. In one embodiment, the method comprises:
a. monitoring the body of water for the presence of veligers and/or early stage bivalves;
b. when an increase in the concentration of veligers and/or settlement stage bivalves is detected, introducing chlorine anion into the service water of the service water system in an amount sufficient to obtain a steady state chlorine anion concentration of 0.1 to 2.0 mg/l;
c. maintaining the steady state concentration of chlorine anion in the service water of the service water system for 10 to 40 days.

In one embodiment, the method further comprises:
d. monitoring a live colony of the bivalves in the service water of the service water system or under chlorine anion concentrations and temperatures comparable to those in the service water system and terminating treatment after the bivalves in the live colony die.

In one embodiment, the chlorine anion is introduced in the form of an aqueous solution of a hypochlorite salt, for example as a solution of a metal hypochlorite salt such as aqueous NaOCl.

The chlorine anion may be introduced at a single location, such as the water inlet to the service water system, or at multiple locations in the service water system.

In one embodiment, chlorine anion is introduced into the service water of the service water system in an amount sufficient obtain a steady state chlorine anion concentration of from 0.1 to 2.0 mg/l, preferably from 0.2 to 1.0 mg/l and more preferably from 0.40 to 0.80 mg/l.

In one embodiment, the method further comprises analyzing the chlorine anion concentration in the service water and increasing or decreasing the amount of chlorine anion introduced into the service water in order to maintain the steady state chlorine anion concentration.

In one embodiment, the method further comprises neutralizing residual chlorine in an effluent from the service water system such as by use of a neutralizing agent such as a sulphur-based compound. In one embodiment the chlorine neutralizing agent is sodium bisulphite.

In one embodiment, one or more live colonies of bivalves in the service water of the service water system or under chlorine anion concentrations and temperatures comparable to those in the service water system are monitored. In one embodiment, the method includes:
i. seeding a water permeable container with a sample of live bivalves;
ii. acclimatizing the live bivalves to ambient conditions of the service water;
iii. placing the container in the service water of the service water system or in water that has chlorine anion concentrations and temperatures comparable to those in the service water system; and,
iv. determining the viability of the bivalves in the container, wherein bivalve mortality is correlated with the effectiveness of the treatment.

In one embodiment, the method is performed only in spring after an increase in the concentration of veligers is detected. In one embodiment, the method is performed only in fall after an increase in the concentration of settlement stage bivalves is detected.

In another aspect, there is provided a method for controlling bivalve growth in a service water system of a plant wherein service water generally continually flows from a water supply inlet to a water supply outlet. In one embodiment, the method comprises:
a. introducing chlorine anion into the service water of the service water system at a concentration sufficiently high to kill early stage bivalves and sufficiently low such that the early stage bivalves continue to respire and ingest chlorine; and
b. maintaining the concentration of chlorine anion in the service water of the service water system for 10 to 40 days.

In one embodiment, the concentration of chlorine anion is from 0.1 to 2.0 mg/l or any range therebetween. Preferably, the range is from 0.2-1.0 mg/l, more preferably from 0.2-0.8 mg/l and most preferably from 0.4-0.8 mg/l.

In one embodiment, the method further comprises monitoring a body of water from which the water for the service water system is drawn for the presence of veligers and/or settlement stage bivalves and performing the method when an increase in the concentration of veligers and/or early stage bivalves is detected.

In one embodiment, the chlorine anion is introduced in the form of an aqueous solution of a hypochlorite salt, for example as a solution of a metal hypochlorite salt such as aqueous NaOCl.

The chlorine anion may be introduced at a single location, such as the water inlet to the service water system, or at multiple locations in the service water system.

In one embodiment, the method further comprises analyzing the chlorine anion concentration in the service water and increasing or decreasing the amount of chlorine anion introduced into the service water in order to maintain the chlorine anion concentration.

Optionally, the method further comprises neutralizing residual chlorine in an effluent from the service water system, such as by use of a chlorine neutralizing agent such as a sulphur-based compound. In one embodiment the chlorine neutralizing agent is sodium bisulphite.

In one embodiment, the method further comprises assessing the effectiveness of the chlorine anion for controlling bivalve growth in the service water system by monitoring a live colony of the bivalves in test water comprising service water of the service water system or water having chlorine anion concentrations and temperatures comparable to those of the service water system, and terminating treatment after the bivalves in the live colony die. In one embodiment, the live colony of the bi-vales is monitored by:
  i. seeding a water permeable container with a sample of live bivalves;
  ii. placing the container in the test water; and
  iii. determining the viability of the bivalves in the container, wherein bivalve mortality is correlated with the effectiveness of the treatment.

In one embodiment, the bivalves are mussels, optionally zebra mussels or quagga mussels.

In one aspect, the methods described herein include two or more separate treatment periods per year. In one embodiment, the separate treatment periods are near the beginning and end of the bivalve's reproductive cycle. For example, in one embodiment, the methods described herein are performed in the spring and in the fall. In one embodiment, a treatment period is initiated after an increase in the concentration of veligers is detected (typically in the spring), which signals the start of the bivalve's reproductive cycle, or shortly thereafter. In one embodiment, a first treatment period is initiated in May, June or July. In one embodiment, a first treatment period is initiated 4-6 weeks after the presence of veligers are first detected in the service water of the service water system. In one embodiment, a treatment period is initiated when an increase in the concentration of pediveligers and/or settlement stage bivalves is detected (typically in the fall), towards the end of the bivalve's reproductive cycle, or shortly thereafter. In one embodiment, the method involves two separate treatment periods and a second treatment period is initiated 8-24 weeks after the first treatment. In one embodiment, a second treatment period is initiated in August, September, October, November or December. In one embodiment, the method is performed only in spring after an increase in the concentration of veligers is detected. In one embodiment, the method is performed only in fall after an increase in the concentration of settlement stage bivalves is detected.

It will be appreciated that each of the embodiments is optional and any aspect disclosed herein may be used with any one or more of the possible embodiments disclosed herein and accordingly the various embodiments may be used in any combination or sub-combination.

DETAILED DESCRIPTION

Figure 1:
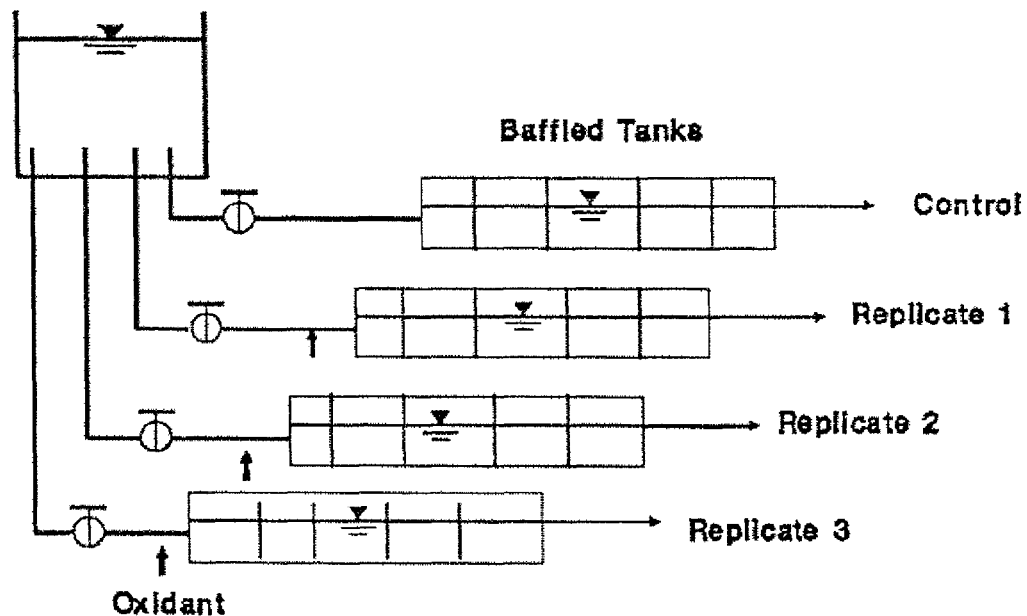
FIG. 1 shows the baffled tank experimental apparatus for the chlorine experiments described in Example 2.

In one aspect, the present description provides a method for controlling bivalve growth in a service water system of a plant. The method is particularly useful for controlling bivalve growth in service water systems where water continuously flows through the system. In one embodiment, the service water generally continuously flows from a water supply inlet to a water supply outlet to provide, e.g., cooling or any equipment in a plant. Water may be drawn into the service water system from a body of water by gravity, pumping water into the system, or combinations thereof.

Service water systems are commonly used to provide a source of service water for the operation and/or maintenance of other systems or machinery within a plant. Examples of plants include, but are not limited to, water treatment plants, power plants, foundries, steel mills or factories. Service water systems may be used for cooling and/or heat transfer in the plant.

It will be appreciated that the method disclosed herein may be used in addition to any other treatment applied to water drawn from the body of water, such as any filtration or purification treatment that may be known in the art.

As used herein "body of water" refers to a body of water such as a natural or artificial lake, river, stream, well or reservoir that is capable of supporting the growth of bivalves. In a preferred embodiment, the volume of the body of water is significantly larger than the volume of the service water system of the plant.

As used herein, "bivalve" refers to a class of molluscs that have a laterally compressed body enclosed by a shell in two hinged parts. The methods described herein are particularly useful for the control of freshwater bivalves. In a preferred embodiment, the bivalves are mussels, optionally zebra mussels (*Dreissena polymorpha*) and/or quagga mussels (*Dreissena bugensis*).

As used herein "controlling bivalve growth" refers to preventing or inhibiting the settlement and/or colonization of bivalves and optionally includes killing the bivalves.

In one embodiment, the method described herein includes monitoring water from which the service water is drawn and/or the water in the plant (e.g., the body of water and/or the service water in the service water system) for the presence of veligers and/or settlement stage bivalves so that treatment may commence when early stage bivalves are detected. The presence of veligers and/or settlement stage bivalves can readily be detected and monitored such as by visual inspection of water samples from the body of water or service water system, or by inspecting surfaces exposed to the body of water or service water system or by other methods known in the art. As used herein, visual inspection optionally includes the use of detection equipment that can be used to recognize the presence of veligers and/or settlement stage bivalves such as a magnifying device such as a microscope, an image recognition system that analyzes images from a camera, or the like.

Preferably, in some embodiments the method disclosed herein is used when veligers and/or early stage bivalves are detected, which signals the start of the reproductive cycle. In one embodiment, the method disclosed herein is used only when an increase in the concentration of pediveligers and/or settlement stage bivalves is detected. Accordingly, in one embodiment, the body of water and/or service water is periodically monitored for the presence of veligers, pediveligers and/or settlement stage bivalves. Optionally, the methods disclosed herein include two or more separate treatment cycles per year. In one embodiment, the body of water and/or service water is periodically monitored commencing near an expected start date of the reproductive cycle of the bivalve, such as when the water reaches a predetermined temperature in the spring which is indicative of the start date of the reproductive cycle. In one embodiment, a treatment cycle is performed when an increase in the concentration of veligers is detected (typically in the spring), which signals the start of the bivalve's reproductive cycle, or shortly thereafter. In one embodiment, the body of water and/or service water is periodically monitored commencing near the expected first appearance of pediveligers in the body of water, typically in late August to October. In one embodiment, a treatment cycle is performed when or after an increase in the concentration of pediveligers and/or settlement stage mussels is detected (typically in the fall), towards the end of the bivalve's reproductive cycle. Optionally, a treatment cycle may be performed in the spring and the fall, only in the spring or only in the fall depending e.g. on the prevalence of bivalves and the tolerance of the service water system.

As used herein, "veligers" refers to the early stage planktonic form of zebra mussel larvae that develop directly from the egg stage. In one embodiment, the presence of veligers in water samples indicates that the reproductive cycle of zebra mussels has begun, and that settlement is about four to six weeks away. Veligers generally begin to appear in late May to early July or when water temperatures approach 8° Celsius or about 46° Fahrenheit. Veligers typically have a size range of typically about 60-150 μm. As used herein, the term "veliger" optionally includes post-veligers, which represent the second larval stage of the development of the zebra mussel and are typically about 150-200 μm.

As used herein, "settlement stage bivalves" refers to pediveligers, juveniles and/or adult mussels. Pediveligers are an intermediate stage between post-veligers and juveniles. Pediveligers have the ability to both swim and crawl (with a muscular foot). At this stage, pediveligers are actively seeking an ideal place to settle and will release and resettle frequently (called translocation). Pediveligers generally appear in late August to October and are typically about 200-300 μm. Juvenile mussels are a settled, non-reproductive form of zebra mussel that are often visible to the naked eye and have characteristic stripes. Juveniles generally being to appear in September to October and are typically 300 μm-5 mm. As used herein "early stage bivalves" refers to veligers, pediveligers and juvenile mussels.

In one embodiment, upon detection of an increase in the concentration of veligers, pediveligers and/or early stage bivalves, chlorine anion is introduced into the service water of the service water system. By introducing chlorine anion into the service water when an increase in the number of veligers, pediveligers and/or early stage bivalves is detected, the methods of the present invention allow for controlling bivalve growth without the need for continuous treatment of the service water. The inventors have also determined that maintaining a steady state chlorine anion concentration between 0.10 and 2.0 mg/l or any range therebetween (preferably from 0.2-1.0 mg/l, more preferably from 0.2-8 mg/l and most preferably from 0.4-0.8 mg/l) for 10 days to 40 days is surprisingly effective at controlling bivalve growth and preventing undesirable infestations and buildup of bivalve shell debris within flow-through service water systems.

A skilled person will appreciate that whether a treatment cycle should be initiated in response to an observed change in the concentration of veligers, pediveligers and/or early stage bivalves will depend on the operational tolerance of a particular service water system. For example, small fluctuations in the level of veligers, pediveligers and/or early stage bivalves may or may not represent an increase such that the introduction of chlorine anions according to the methods described herein is warranted. In a preferred embodiment, a treatment cycle is initiated when an increase is the number of veligers and/or early stage bivalves is detected that suggests the start of the reproductive cycle or the flow of non-settled bivalves into the service water system. In one embodiment, a treatment cycle is initiated when an increase in the number of pediveligers or settlement stage bivalves is detected. In one embodiment, two or more treatment cycles are performed over the course of one year at a service water system. In one embodiment, a first treatment cycle is initiated when an increase in the number of veligers is detected and a second treatment cycle is initiated 8-24 weeks after the first treatment cycle. In one embodiment, a second treatment cycle is performed when increase in the concentration of pediveligers and/or settlement stage mussels is detected (typically in the fall), towards the end of the bivalve's reproductive cycle. In one embodiment, a first treatment cycle is initiated in May, June or July, and a second treatment cycle is initiated in August, September, October, November or December. In one embodiment, a second treatment cycle is initiated at least about 16 weeks after the initial appearance of veligers is detected in the spring.

In one embodiment, chlorine anion is introduced in an amount sufficient to obtain a steady state chlorine anion concentration of about 0.10 to 2.0 mg/l in the service water of the service water system, or any range therebetween. Preferably the range is from 0.2-1.0 mg/l, more preferably from 0.2-8 mg/l and most preferably from 0.4-0.8 mg/l. The amount of chlorine anion may be sufficient to obtain a chlorine anion concentration of about 0.1 mg/l, 0.2 mg/l, about 0.3 mg/l, about 0.4 mg/l, about 0.5 mg/l, about 0.6 mg/l, about 0.7 mg/l, about 0.8 mg/l, about 0.9 mg/l, about 1.0 mg/l, about 1.2 mg/l, about 1.4 mg/l, about 1.6 mg/l about 1.8 mg/l or about 2.0 mg/l. Exemplary ranges include a steady state concentration between 0.2 mg/l and 0.5 mg/l or between 0.5 mg/l and 1.0 mg/l.

In one embodiment, the methods described herein include introducing chlorine anion into the service water of the service water system at a concentration sufficiently high to kill early stage bivalves and sufficiently low such that the early stage bivalves continue to respire and ingest chlorine. As shown in Example 2, levels or chlorine anions as low as 0.1 mg/l are useful for inhibiting the settlement of veligers and early stage bivalves and cause veligers to retract their vellum. Furthermore, concentrations of chlorine anions between 0.1 mg/l and 0.3 mg/l are sufficiently low that the veligers continue to respire but sufficiently high that to cause toxicity such that bivalves exposed to for periods between 10 and 40 days are likely to die.

The chlorine anion may be introduced into the service water in different forms. For example, in one embodiment the chlorine is introduced as an aqueous solution of a hypochlorite salt, such as aqueous sodium hypochlorite. Optionally the chlorine anion is introduced in the form of gaseous chlorine. A skilled person will appreciate that solutions of chlorine in water contain chlorine ($Cl_2$), hydrochloric acid (HCl), and hypochlorous acid (HClO). In aqueous solution, hypochlorous acid partially dissociates into the anion hypochlorite ClO⁻.

As used herein, "chlorine anion" refers to anionic compounds that contain chlorine such as, but not limited to, oxyanions and other species of free and residual chlorine. In a preferred embodiment, the chlorine anion is introduced as an ionic compound that contains oxygen such as a chlorine oxyanion. In one embodiment, the chlorine oxyanion is hypochlorite ($ClO^-$), chlorite ($ClO_2^-$), chlorate ($ClO_3^-$) or perchlorate ($ClO_4^-$). In a preferred embodiment, the chlorine anion is a hypochlorite, optionally sodium hypochlorite (NaOCl) or calcium hypochlorite $Ca(OCl)_2$.

Remarkably, while Canadian Patent Application No. 2,091,928 reported that NaOCl (sodium hypochlorite) and $NaClO_2$ (sodium chlorite) did not achieve acceptable mortality rates in continuous 24 hour treatments relative to chlorine dioxide, the present inventors have determined that treatment of service water with chlorine oxyanions such as sodium hypochlorite is highly effective for inducing toxicity and/or inhibiting settlement of early stage bivalves.

In one embodiment, the method comprises maintaining a steady state concentration of chlorine anion in the service water of the service water system for 10 to 40 days, or any range therebetween. Preferably, the range is from 15-30 days and may be 10 to 15 days, 14 to 30 days, 15 to 35 days, or to 40 days. In one embodiment, the duration of treatment with chlorine anion depends on the temperature of the water. Bivalves in bodies of water at lower temperatures generally require longer treatment times to control growth of the population than bivalves in warmer water. For example, when the water temperature is less than about 15° Celsius, bivalves uptake chlorinated water much more slowly, which extends the time required to achieve complete mortality.

Various methods known in the art are useful for maintaining a steady state concentration of chlorine anions in the service water of the service water system. For example, in one embodiment the volume and flow-through rate of the service water system is used to determine an amount of chlorine anion to be introduced into the system to obtain the desired concentration or steady state concentration of chlorine anion. In a preferred embodiment, chlorine anion is continuously or periodic introduced into the service water as additional water is drawn from the body of water and flowed through the system. In one embodiment, the chlorine anion concentration is analyzed in the service water system and the method includes increasing or decreasing the amount of chlorine anion introduced into the service water in order to maintain the concentration or steady state concentration.

In one embodiment the methods described herein include a ramp-up period that precedes steady state chlorination. As used herein, "ramp up period" refers to a period wherein chlorine anions introduced into a service water system are largely absorbed by the initial chlorine demand of the service water system. The use of a ramp up period enables operators to maintain precise control of chlorine residuals in the service water system and minimizes the presence of detectable residuals at the effluent sites. Furthermore, the use of a ramp-up period avoids over-chlorination after the "breakpoint" stage has been reached. Breakpoint is the point at which all readily-reacted substances have been reacted with the oxidizer, including organics and inorganics in the flowing water as well as material on the physical surfaces such as slime and algae build up and there is a sudden and sometimes dramatic increase in free available chlorine. This breakpoint could occur at any time, and ramping up incrementally with sufficient stabilization periods between pump adjustments reduces or sometimes eliminates the severity of the residual peak after breakpoint is reached.

For example, in one embodiment one or more chlorine analyzers are used to monitor chlorine anion levels in the service water system. Preferably, the chlorine analyzers are downstream of sites where chlorine is introduced into the service water system. Optionally, the analyzers detect total residual chlorine (TRC) levels in the service water. In one embodiment, a signal from the analyzer is transmitted to a controller, such as a programmable logic controller (PLC) which compares the analyzer value to a pre-determined set point. The controller is optionally connected back to one or more devices such as portable injection systems for introducing chlorine anion into the service water. In one embodiment, the controller then increases or decreases the amount or rate of introduction of chlorine anion to maintain the target steady state chlorine anion concentration. Optionally, the introduction of chlorine anion into the service water system can be manually adjusted based on data from a chlorine analyzer or from the monitoring a live colony of bivalves. In one embodiment, the controller simultaneously transmits data from the chlorine analyzer value to a secondary recording device providing a permanent record of TRC trends. In one embodiment, one or more chlorine analyzers are used to monitor chlorine levels during the ramp-up period.

In one embodiment, additional chlorine analyzers interfaced with circular paper chart recorders or electronic data loggers are installed at various sites in the service water system so that dosing trends can be tracked throughout critical areas of a given plant facility. The recorded data may be used to monitor the levels of chlorine anions in the service water system over time. In one embodiment, the recorded data is useful for ensuring compliance with environmental regulations and/or ensuring that a predetermined level of chlorine anions are maintained in the service water system over time.

In one embodiment, chlorine anion is introduced at one or more locations in the service water system. For example, in one embodiment existing access points or ducts in fluid communication with the service water system may be used to introduce chlorine anions into the service water system. Preferably, at least one of the locations is at or near the water supply inlet from the body of water.

In one embodiment, chlorine anion is introduced to the service water system using one or more injections systems. Preferably, the injection system is or comprises a portable injection system. Accordingly, when treatment is required, the injection system may be brought to the plant, such as in a truck or a trailer and, upon completion of a treatment cycle, the truck or trailer may be optionally removed from the plant.

The injection system may comprise a storage container for the source of the chlorine anions and a dosing system for continuously or periodically injecting chlorine anions into the service water. The injection system preferably also includes one or more analyzers for monitoring the concentration of chlorine anions in the service water.

If the chlorine anions are introduced into the service water in the form of gaseous chlorine, then the container may be pressurized gaseous chlorine. If the chlorine anions are introduced in the form of a compound such as such as sodium hypochlorite, then the container may be any suitable storage container for the solid or liquid compound. It will also be appreciated that the compound may be generated on site such as by reacting two or more reagents together, each of which may be stored separately. The container may be a portable spill storage tank, such as a polyethylene storage tank. Storage tank sizes vary with the scope of the method and are preferably sized to contain 130% of the expected reagent that will be required but may be smaller and may be refilled or replaced from time to time during a treatment cycle.

The dosing system may be any suitable equipment for delivering a predetermined quantity of the chlorine anion into the service water. In one embodiment, the dosing system for introducing chlorine anion into the water system comprises a diaphragmatic metering pump, a peristaltic pump, positive displacement pump, gravity feed, an eduction device, such as a Venturi injector or any delivery device suitable for delivering chlorine anion with flow verification or measurement.

In one embodiment, the methods described herein include monitoring one or more live colonies of the bivalves in the service water of the service water system (e.g., a colony placed in a container in the service water wherein the container permits the flow through of the service water such that the water in the container is comparable to that of the service water at that location in the system) or under conditions comparable to those in the service water (e.g., conditions that are comparable to those in the service water with respect to chlorine anion concentrations and temperature). Accordingly, one or more observation tanks containing a live colony may be provided in the truck or trailer. The tank is filled with water that is either drawn from the treated service water or which is separately treated to mimic the conditions of the treated system water. The colony may be drawn from the service water or the body of water. The monitoring of the live colony may be used to determine when to terminate treatment. For example, treatment of the service water with chlorine anion may be terminated when a desired reduction in colony number or death of a live colony is observed in the observation tank or a set time after the desired reduction or death is observed.

Monitoring a live colony of bivalves in the service water of the service water system, or under comparable conditions, provides a number of advantages. In one embodiment, monitoring a live colony of bivalves allows for the system operator to gauge the success of the treatment and to make changes to the treatment conditions or duration of the treatment. Accordingly, the observation tank may be used to control the treatment or as a back-up to check that predetermined treatment conditions are successful. Accordingly, terminating treatment when the observed live colony of bivalves is killed or reduced to acceptable levels prevents discontinuing treatment too early before the desired level of control or eradication of the bivalves is achieved. Furthermore, terminating treatment when the live colony of bivalves is killed or reduced to acceptable levels prevents overtreating the service water system and the discharge of unnecessary amounts of chlorine, so as to avoid an environmental impact or comply with local discharge requirements.

Different positions in the service water system may experience different conditions with respect to temperature and/or variations in chlorine anion levels. Therefore, instead of using a single observation tank or observing a contained colony in one location of the service water system, a plurality of live colonies of bivalves may be placed and monitored at different positions in the service water system or in a plurality of tanks mimicking the conditions at different locations in the service water system. Accordingly, in one embodiment monitoring one or more live colonies of bivalves at different positions within the service water system, or under comparable conditions, permits the success of the treatment to be monitored throughout the service water system.

It will be appreciated that a colony of bivalves that is already present in the service water system or which is seeded in the service water may be monitored during treatment of the service water in the service water system. Alternately, a live specimen bioassay seeded with bivalves may be monitored (such as in an observation tank) under comparable conditions.

For example, in one embodiment the methods described herein include seeding a water permeable container with a sample of live bivalves. Preferably, the sample of bivalves is first acclimatized to ambient conditions of the service water. For example, the sample of bivalves may be placed in untreated water for at least 24 hours prior to placing the sample of bivalves in the service water of the service water system or service water with chlorine anion concentrations and temperatures comparable to those in the service water system. Accordingly, the flow through container may be placed in the service water of the service water system or the live colony may be placed in an observation tank having water that has chlorine anion concentrations and temperatures comparable to those in the service water system. The viability of the bivalves may be determined, such as by determining the number of live bivalves in the container or observation tank. Bivalve mortality is correlated with the effectiveness of the treatment. For example, the mortality of the bivalves that are being monitored may be used to modify and/or terminate the treatment of the service. In one embodiment if the bivalves that are being monitored are killed, the treatment of the service water is terminated. In one embodiment, if the bivalves that are being monitored are not killed within a specific time period following the start of treatment, such as 20 days, 25 days or 30 days, the amount of chlorine anion introduced into service water of the service water system may be increased.

The bivalves may be monitored at least once during the treatment of the service water system. Preferably, the bivalves are monitored periodically such as every day, every 2 days, every 3 days, every 4 days, every 5 days, every 6 days or every 7 days, or combination thereof, during the treatment. Optionally, the bivalves are monitored periodically after 10 days of treatment, after 15 days of treatment, or after 20 days of treatment.

Bivalve mortality can readily be monitored and determined using methods known in the art. For example, bivalve mortality may be determined by a lack of response of the bivalve to gentle prodding, by physical features such as the presence of a gapped open shell or the like.

As used herein, a "colony" refers to two or more bivalves, preferably 10 or more, 50 or more, about 100 bivalves or greater than about 100 bivalves. Preferably, a statistically significant number is used. In one embodiment, the colony is a colony of zebra mussels and/or or quagga mussels. In one embodiment, the colony is attached to a surface. Optionally, the colony includes one or more veligers and/or settlement stage mussels and preferably essentially comprises such mussels.

In another aspect of the disclosure, residual chlorine is neutralized in an effluent from the service water system. As used herein, "neutralizing" refers to incorporating chlorine anion into a stable, non-reactive compound such that it is no longer available to act as an oxidizing agent in solution. Neutralizing residual chlorine further diminishes the environmental impact of the method described herein. In one embodiment, residual chlorine in effluent from the service water system may be treated by exposing the effluent to ultraviolet light or sunlight, such as in a holding lagoon or pond. In one embodiment, effluent from the service water system can be chemically treated to neutralize residual chlorine. For example, sulphur-based compounds such as sodium bisulphite ($NaHSO_3$) or sodium thiosulfate ($Na_2S_2O_3$) may be useful for neutralizing residual chlorine in service water. Other chemical treatments useful for neutralizing residual chlorine include, but are not limited to, ascorbic acid, hydrogen peroxide, oxalic acid, sodium sulfite and sodium nitrite. In one embodiment, the residual chlorine is neutralized using dechlorinating agents and/or adsorbents, such as sulfur dioxide, sulfites, bisulfites, metabisulfites and thiosulfites or granular, solid block and powdered activated carbon. An advantage of the methods disclosed herein is that lower concentrations of chlorine may be used, and may be used for shorter periods of time. Accordingly, if neutralization is desired or required, then the amount of chemicals used in such neutralization may be reduced, thereby reducing the risk that using an excess of the neutralizing chemical may itself pose an environmental threat.

The neutralization step may be conducted using one or more dechlorination systems, optionally portable dechlorination systems, that may be set up to deliver, e.g., a sodium bisulphite solution (SBS) or the like in sufficient quantities, preferably at or upstream of the outlet from the service water system, to meet effluent total residual chlorine (TRC) requirements in the final effluent. The rate of SBS delivery can be calculated based on flow at the effluent site and anticipated chlorine residuals. Optionally, SBS into the effluent can be fine-tuned by manually adjusting the dosing rate once steady state TRC levels are achieved. Preferably, the dosing system is operated in a manner which ensures that there is no substantial overfeed of chemical due to the fact that SBS is an oxygen scavenger and if significantly overfed, will reduce dissolved oxygen levels. In one embodiment, the dechlorination system is manually controlled system based on the loading of TRC in the effluent, as determined through grab sample analysis. Optionally, the chlorine anion in the effluent from the service water system is adjusted in such a manner that all TRC is neutralized while meeting the effluent TRC and dissolved oxygen compliance requirements.

Optionally, compliance sampling at designated service water system effluent site(s) is completed to verify that residual chlorine is not entering the receiving water body and that other required effluent parameters are within acceptable limits. In one embodiment, the methods described herein further include demonstrating compliance in effluent water through the collection and analysis of grab samples.

Example 1

Control of Mussels at a Plant Service Water System

The method described herein for controlling bivalve growth in service water was tested and implemented at a plant that draws raw water from a lake through an inlet channel that feeds a series of pumphouses and an Old Water Treatment Plant (OWTP). Water from the pumphouses is delivered throughout each respective unit of the low pressure service water (LPSW) systems before discharge into a condenser cooling water (CCW) duct. Water from the OWTP is delivered to a new water treatment plant (NWTP) through the common service water system (CSW) prior to discharge into the common CCW duct. Effluent exiting the CCW duct discharges into the lake.

Chlorination

Portable NaOCl injection systems were installed, at three points in the service water system. NaOCl was injected into each service water system and was assisted with carrier water at each of the dosing sites.

Capital Controls model 1870E amperometric chlorine analyzers were installed at each injection facility to monitor TRC levels entering the plant water systems. To automatically maintain adequate TRC levels, the analyzer relayed a signal to an ABB Commander 1900 series Controller that paced a ProMinent™ diaphragmatic metering pump accordingly at each NaOCl dosing site. The controllers' chart recorder component tracked TRC levels entering the water distribution system at all three injection locations.

Analyzers were also installed at the three different biobox sites in the service water system to monitor TRC (Total Residual Chlorine) concentrations within the plant water systems. The analyzers relayed signals to ABB SM500F video graphic recorders to provide a continuous record of TRC concentrations throughout the duration of the chlorination treatment.

Dechlorination

A portable dechlorination system was installed at a discharge point of the service water system. The dechlorination system consisted of three spill contained polyethylene storage tanks with 13,250 L total capacity and a portable dosing panel.

Sodium bisulphite solution (SBS) was manually injected with carrier water assist into the effluent stream to remove trace TRC from the effluent prior to discharge into the lake. Using a ProMinent Sigma diaphragmatic metering pump, the dose rate was predetermined based on site specific flow calculations.

Effluent Monitoring

Daily grab samples were collected from the plant outfall, and analyzed for TRC and Dissolved Oxygen (DO). Grab samples were analyzed for TRC using a Wallace and Tiernan Series A-790 amperometric titrator and for DO using a Hach dissolved oxygen test kit (model OX-2P).

Bioassay

Bioassays were conducted to monitor the effectiveness of the chlorination program. One hundred adult mussels contained in mesh bioassay baskets were placed in bioboxes at three separate locations in the service water system. Throughout the treatment, mussels were inspected daily for mortality, indicated by gaping and non-response to probing. Water temperature observations were also recorded on a daily basis. The purpose of a bioassay is to simulate conditions within the water systems and to provide an indication of when mussels succumb to treatment. Complete mortality in bioassays is indicative of the success of a treatment at eradicating mussels from the piping systems.

Results

Sodium hypochlorite (NaOCl) (nominal 12 wt % aqueous) was injected at a rate of 1500 ml/min into the CSW, and at the low pressure service water systems (LPSW) at two different sites at respective rates of 700 and 775 ml/min, later increased to 1000 ml/min, through respective travelling screen forebays.

SBS (24% aqueous) was injected with carrier water assist into the final plant effluent. SBS entered the discharge stream upstream of the final effluent sampling point to neutralize any trace total residual chlorine (TRC).

Throughout the treatment, TRC levels at the plant discharge did not exceed 0.010 mg/l and dissolved oxygen levels were greater than the minimum compliance requirement of 4.0 mg/l as sampled and detected by ASI personnel.

Bioassays were conducted during the treatment to determine mortality rates throughout the system. Complete mortality was observed in Unit 0 on Day eighteen (18) of the treatment. Unit 3 and 4 observed complete mortality on Day twenty three (23) of the treatment. Water temperatures fluctuated throughout the treatment averaging 10° C. Overall, the two treatments per season employed at the plant facility ensured that the facility has remained free of long term infestation and has significantly reduced the risk of line blockages due to shell debris.

Example 2

Effect of Chlorine Anion Oxidants on Veligers and Juvenile Mussels

Summary

This example provides results of a study examining the effects of a chlorine oxidant on the inactivation of zebra mussel veligers. In addition to the work that was undertaken for veligers, an evaluation of the impact of chlorine on juvenile zebra mussels was also made.

At doses over 0.1 mg/l, over 97% reduction in veliger numbers were observed in tanks receiving chlorine compared to controls. Increases in chlorine and doses above 0.2 mg/l did not appear to produce greater inactivation. This result implies that only a threshold concentration of oxidant is needed to cause veligers to retract their vellum and become "inactivated."

Examination of sediments collected in the baffled tanks during each study showed that veligers exposed to oxidants were removed from the water column by gravity sedimentation. In sensing the presence of an oxidant, veligers retracted their vellum and were removed to the sediments in the relatively quiescent flow conditions in the baffled tanks. In systems with higher velocities, veligers that react to oxidants in a similar fashion may remain suspended and be removed without settling.

Continuous application of chlorine at 1 mg/l at 8 to 12° C. was required for over 25 days to kill juvenile zebra mussels ranging in size from 0.75 to 5 mm. Based on studies involving adult zebra mussels, shorter contact times would be expected at warmer temperatures. The ability to kill juvenile mussels suggests that if a strategy aimed at controlling veligers fails and some settlement occurs, prolonged exposure to oxidants will kill recently settled mussels.

The results of this study suggest that the oxidant may not have to kill veligers to prevent settlement. While the ability of the mussel to sense the presence of an oxidant makes treatment more difficult in the case of adults, this same trait in veligers may cause them to flow through a system without settling.

Methodology and Experimental Setup

All experiments were conducted at a County Water Authority's water treatment plant. A continuous supply of approximately 29,000 liters per day (7600 US gal/day) was needed to carry out this work. Raw water for the study was obtained by tapping into the main water conduit as it entered the plant. An existing unused polymer injection line was plumbed with a ¾ in (18 mm) schedule 40 PVC pipe. A water shut off valve was put at the point where the PVC pipe coupled with polymer line so that the entire system could be dewatered if necessary.

The 18 mm PVC water supply line was plumbed into a manifold system which fed three 60 liter constant head tanks, each fitted with standpipe overflow drains. Ball valves were installed at the point of inflow allowing for better flow control. Four 30 liter baffled tanks were fed from each constant head tank (see FIG. 1). Flow to each baffled tank was controlled by a 12.5 mm (½ in) ball valve installed at the base of the head tank. Equal length (approximately 915 mm or 36 inches) 12.5 mm Tygon tubing delivered raw water (containing veligers) from the constant head tanks to the baffled tanks.

Figure 2:
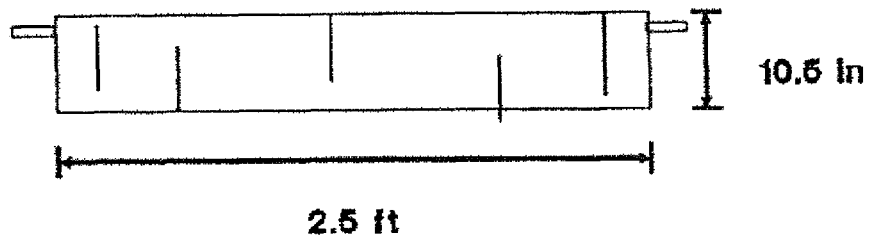
FIG. 2 shows a plan view of the baffled tank design used for the experiments described in Example 2.

A fifth outflow valve for obtaining veliger density samples was fitted to each constant head tank. The baffled tanks were constructed of plexiglass and had dimensions of approximately 762 mm×300 mm×264 mm (2.5×1×0.88 ft). Each tank was fitted with 5 alternating vertical baffles (see FIG. 2). The flow rate through the tanks was maintained at 1 l/min. The alternating baffles produced a serpentine flow through the tanks with a mean calculated hydraulic residence time of 30 minutes. The effluent of the tanks drained into a collection system and discharged into a sump.

Application and Measurement of Oxidants

For all experiments, each group of four baffled tanks was considered one experimental unit. One of the baffled tanks was utilized as a control and received no oxidant while the other three served as replicates for a given oxidant dose.

Chlorine

Chlorine stock solutions were prepared by diluting aqueous sodium hypochlorite in filtered raw water. A variable speed peristaltic pump was utilized to continuously pump the stock solution into the system. Injection tees were fabricated from 12.5 mm (½ in) PVC tee fittings and small glass tubing. The tees were spliced into the Tygon tubing approximately half-way between the constant head tank and the baffled tank. This point of injection insured the mixing of stock chlorine solution and raw water before entering the experimental baffled tanks.

Total chlorine residual concentrations were measured using a portable flow through amperometric chlorine analyzer (Capitol Controls). Chlorine residuals in the baffled tank effluent were measured on a daily basis. Chlorine residual concentrations also were measured at various points in the baffled tanks. The chlorine concentrations in the water between the baffles also were spot checked to see if the residual concentrations decreased through the tanks. On several occasions, the chlorine analyzer data were collected with an electronic data logger to determine if the residual concentrations varied over 24 hour periods. The data logger took readings every five seconds and produced ten minute averages which were stored in memory. These data then were down loaded onto a floppy disk for analysis.

The effect of chlorine on veligers was tested at five nominal total chlorine residual concentrations: 0.1, 0.2, 0.5, 0.75 and 1.0 mg/l. Because the inhibition of settlement was one objective of these tests, the experiments were run for seven days.

The effect of chlorine on juvenile mussels was carried out at a nominal total chlorine residual of 1.0 mg/l.

Determination of Raw Water Veliger Density

The first access to the raw river water was in the constant head tanks of the experimental system. Experimental baffle tanks were fed from the constant head tanks. Therefore, the density of veligers entering the system was monitored from the constant head tanks. Each constant head tank had a valved port for sampling. From this port, 40 to 60 liters of raw water were passed through an inline sampler with a plankton sampling bucket having a mesh size of 63 microns. This sampler allowed the large volume of raw water to be concentrated to approximately 50 ml. For greater accuracy, the 50 ml volume was concentrated further to approximately 20 ml by passing the sample through a sieve (53 μm mesh).

The number of veligers in four or five subsamples was counted using a Sedgewick-Rafter counting cell. Before removing a 1 ml subsample for counting, the 20 ml sample was homogenized by gently swirling. The number of veligers in the subsample was counted under a magnification of 40×. Four or five subsamples of the sample were counted insuring that 20 to 25% of the sample was counted. These samples were considered adequate because the variance among subsamples was low, with the coefficient of variation ranging from 4 to 17 percent. One complete counting of a sample to test the method found that after 5 subsamples the mean number of veligers was 6.2 $L^{-1}$ and dropped to 5.7 $L^{-1}$ after 22 subsamples. This test was not repeated at higher veliger densities.

From the mean number of veligers in the subsamples an estimate of the actual veliger density was calculated as follows:

$$\text{Density (\#/L)} = \frac{\text{(mean of subsamples)} \times \text{(vol. of concentrated sample)}}{\text{(vol. of raw water concentrated)}}$$

On several occasions, the three constant head tanks were all sampled within one hour of each other. The density estimates were consistent for all three tanks.

Effluent Veliger Density Determination

One method of determining the fate of the veligers passing through the baffled tanks was based on sampling the tank effluent. This was done by placing a fine mesh sieve (initially 74 microns later 63 microns) under the effluent and allowing the effluent to be filtered for 15 to 30 minutes. During chlorination, the time period was 20 to 30 minutes. This time period allowed 20 to 30 liters of water to be filtered.

The material, including veligers, collected in the sieve was resuspended in approximately 20 ml of previously filtered raw water. The concentrated veligers then were counted and densities estimated in the same manner as constant head tank samples.

Frequently, a comparison of the constant head tank densities and the densities found in the control effluents was made. When making these comparisons, the two samples were taken simultaneously. This was necessary because veliger densities of the incoming raw water could change over short time periods. The control effluent densities were always close to the numbers found in the constant head tanks.

Sampling of Settled Veligers

One objective of the oxidant experiments• was to compare the settlement of veligers within the control baffled tanks to the settlement in tanks receiving oxidant. It was possible that veligers would settle on the sides of the plexiglass tanks. However, the tank sides would be very difficult to sample. Removable PVC settling plates that could be marked with a grid and easily subsampled were utilized. These plates were clamped to the front of two baffles in the baffled tanks (see FIG. 2). Each plate was 200 mm (8 in) long and 75 mm (3 in) wide. The water depth in the baffle tanks was approximately 100 mm (5 in). The face of the baffles could accommodate three settling plates providing a settling area of approximately 29,000 $mm^2$ (45 $in^2$). This area was gridded into twelve, 25 mm (1 in)×75 mm (3 in) sampling areas (see FIG. 3).

Three settling areas on each baffle face were sampled at one time. The choice of the area to be sampled was determined by a random number table. Since the settled veligers would be barely visible, the entire surface of the 25 mm (1 in)×75 mm (3 in) unit was scraped utilizing a fine edged spatula. All the material on the surface of the sampled area was transferred to a finely gridded petri dish and examined microscopically (30× magnification).

During the chlorine experiments, the plates were sampled on the 3rd and 7th day of exposure. The duration of the hydrogen peroxide experiment was 14 days. During this experiment sampling occurred on days 3, 7 and 14.

Sediment Analysis

It was discovered during the study that veliger effluent densities in the experimental tanks were much less than the controls. This suggested that veligers had remained in the baffled tanks. One possible location of the veligers was in the sediments that accumulated in the tanks. Therefore, during or after an experiment the sediments were sampled and both dead and alive veligers were counted. Because of the amount of sediment that accumulated and the large number of veligers that passed through the tanks during the test periods, it was not practical to analyze all the sediment that was in the tank at any one time. Subsamples were collected from the bottom area of the tanks at three locations. The objective of the subsampling was to determine the fate of the veligers in the experimental tanks.

Figure 4:
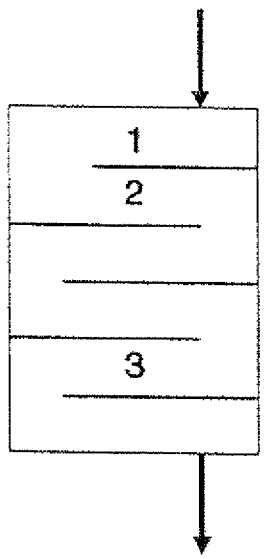
FIG. 4 shows the areas used for sediment sampling in baffled tanks as described in Example 2.

The location of the areas sampled in the tanks is shown in FIG. 4, Area #1 is the first section of the tank that the veligers encountered. However, the veligers had been briefly exposed to oxidants in the Tygon tubing before entering the baffled tanks. Areas #2 and #3 were located in front of the baffles that held settling plates.

The area sampled was 5,810 $mm^2$. This area was isolated by a square plexiglass frame that was lowered slowly into the sediment. The sediment in this square area then was siphoned. Initially, the sediment was sieved in a 53 μm sieve to eliminate the finest sediment and facilitate counting. The sediment then was suspended in approximately 30-50 ml of previously filtered river water. The veligers in this suspension then were counted as described previously. The efficiency of this enumeration procedure was not tested. However, these estimates are considered less accurate than water column sampling. The sediment itself made counting difficult. However, the objective of the sediment analyses was not to obtain accurate density estimates but rather to gain insight to where the veligers were in the tanks.

Juvenile Exposure to Chlorine Experiment

The small size of juvenile mussels (1-5 mm) presented the problem of containment of the animals during exposure to chlorine. Vials perforated with many tiny holes were deemed impractical for two reasons. First, the tiny holes may inhibit the desired circulation of chlorinated water within the vial. Second, the small mussels would be difficult to remove from such vials if they were attached by byssal threads. It was decided that a suitable experimental unit was a small PVC plate that could be colonized by an appropriate number of juvenile mussels. PVC plates could be submerged for uniform exposure and were sampled easily as the small mussels slid off the plates with minimal force.

The mussels were colonized on to plates as two size classes, 0.75-2.0 mm and 2.5-5.0 mm. Due to the mobility of the mussels, it was impossible to colonize an exact number of mussels on each plate. Once colonized and acclimated to the experimental tanks, the mean number of mussels of the 0.75 to 2.0 mm mussels was 25.5/plate (std dev=10.2). The mean for the larger juveniles (>2 mm) was 13.1/plate (std dev=4.7).

Figure 5:
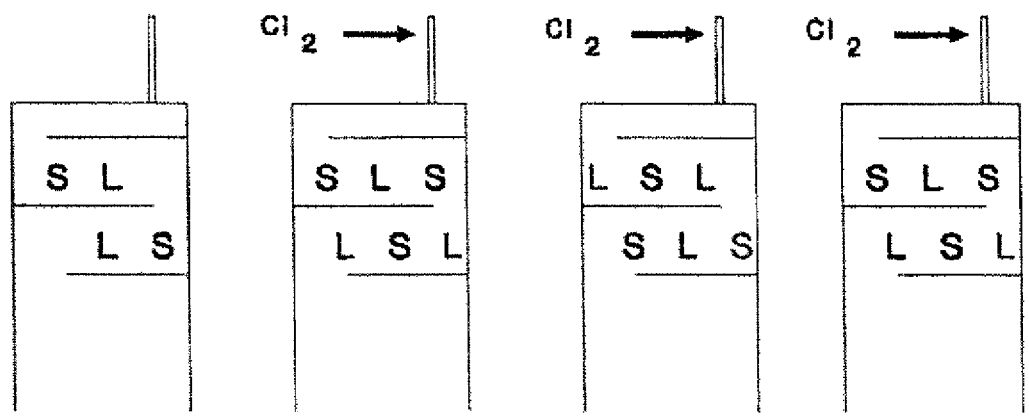
FIG. 5 shows the colonized plates for the juvenile mussel experiments described in Example 2.

The colonized plates were transferred to four baffled tanks. The plates were submerged vertically at a 75° angle, supported by baffles. The base of each plate rested in a petri dish which would collect any dead mussels that fell from the plate during exposure. The plates were arranged so that the two size classes were alternated. Three baffled tanks that received chlorinated water contained six plates. The fourth tank served as a control and contained four colonized plates (FIG. 5). The mussels were allowed to acclimate for 48 hours.

The mussels were subjected to a continuous dose of 1.0 mg/chlorine. The chlorine stock solution was injected into the system before the raw river water entered the baffled tanks.

Mixing was further enhanced by the delay of flow in front of the first baffle. Total chlorine residual concentrations were monitored daily using the portable amperometric chlorine analyzer. The mussels in the control tank were exposed to raw river water only. In the first week of exposure, the mussels appeared viable. Actual sampling did not commence until the 8th day of the experiment. After this plates were sampled every 2 or 3 days.

The sampling procedure involved randomly selecting one plate of each size class from one of the three experimental tanks. The mussels on each plate were manually dislodged from the plate into a separate petri dish. The petri dish that the plate had rested in also was removed from the tank and any mussels in the dish were examined separately. Determinations of living and dead mussels were made under magnification of 10 to 20×. A mussel that was gapped was considered dead. The condition of the other mussels was determined by their activity in the next 24 hours. After being disturbed, juvenile mussels become active in a much shorter period of time than adults. Consequently, most living juveniles showed activity (siphoning or movement) in less than 30 minutes. If a mussel had not moved in a 24 hour period, it was considered dead. Few ungapped mussels were dead. The length of each mussel was measured to the nearest half millimeter.

Raw Water Quality

Raw water quality variables monitored during the study included temperature, pH, and turbidity. Temperature was measured by study personnel from the constant head tanks in the experimental apparatus. Turbidity and pH data were obtained from County Water Authority personnel who monitor these parameters daily in the raw water to the plant.

Results

Raw Water Quality

Figure 6:
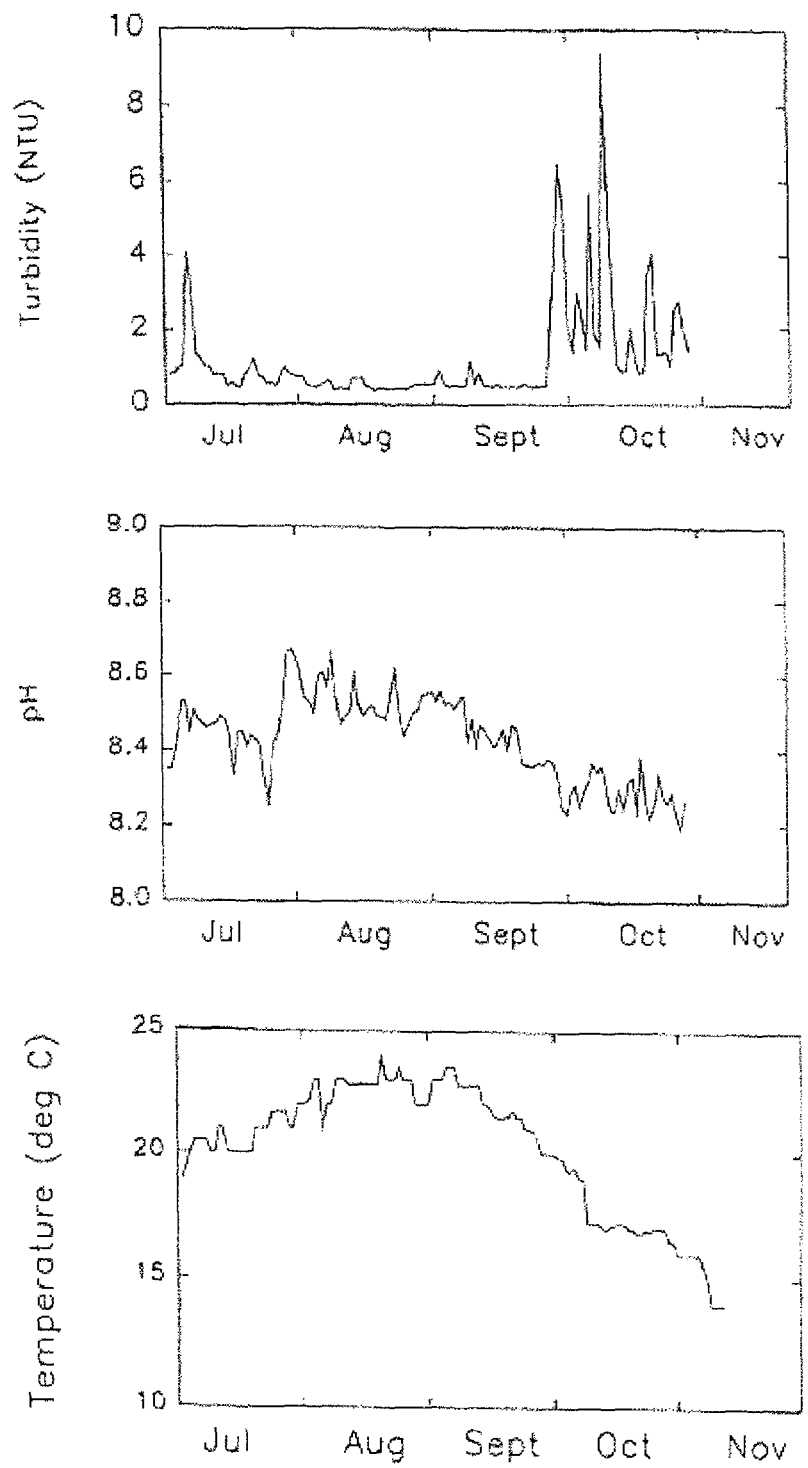
FIG. 6 shows turbidity, pH and temperature data for June to November.

Several water quality parameters measured in the raw water at the Van de Water treatment plant are summarized in Table 1. Total alkalinity and hardness showed very little variation during the period of veliger monitoring. Turbidity, pH and temperature showed seasonal variation. FIG. 6 shows the temporal changes of these three variables during the period of veliger monitoring.

TABLE 1

Water Quality Parameters During Study Period

| Parameter (units) | Mean (standard deviation) | Range |
| --- | --- | --- |
| Turbidity (N1U) | 1.22 (1.4) | 0.3-9.4 |
| Alkalinity (mg/l as CaC03) | 98.1 | 94-100 |
| Hardness (mg/l as CaC03) | 124.1 | 120-126 |

Veliger Densities

Figure 7:
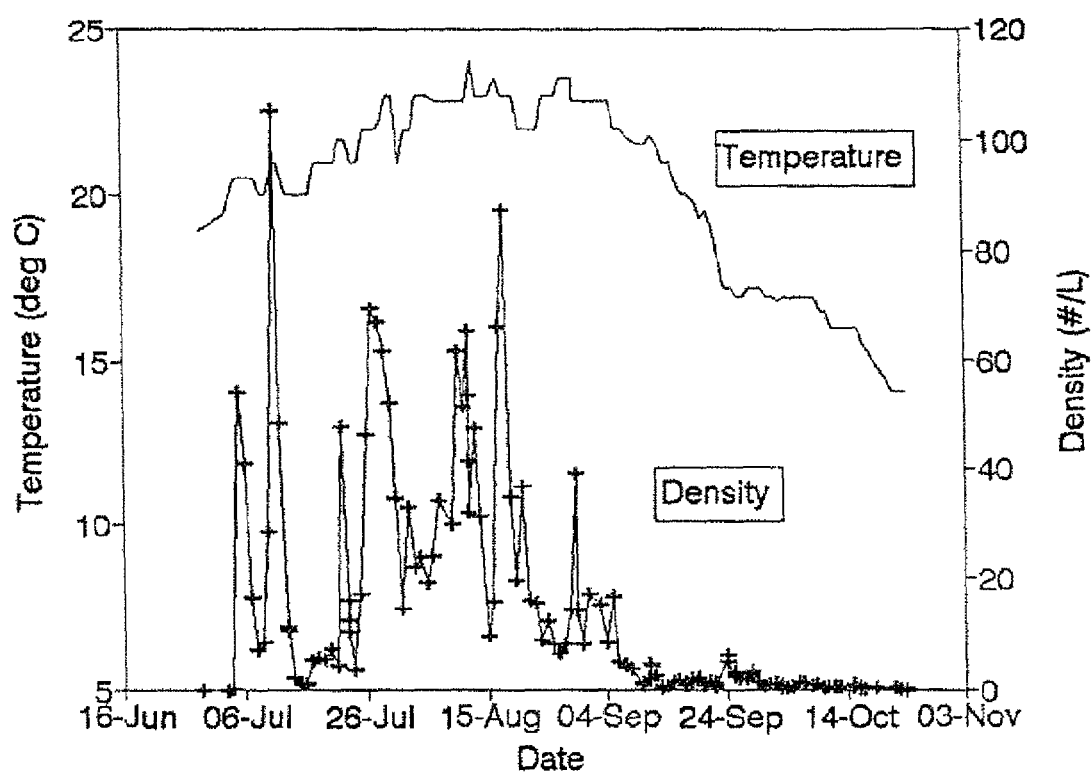
FIG. 7 shows experimental veliger density and water temperature data for June to November.

Monitoring for veligers in water in the constant head tanks commenced on June $29^{th}$. The first veligers were not found in the plankton community until July 7th. FIG. 7 shows the veliger densities and river water temperature from late June through late October. Note the great variability in veliger numbers from early July through August. It should be noted that most of these densities were estimated from one daily sample. Occasionally, a series of samples was taken through the day. It was found that densities changed in a matter of hours. For example, on August 12th five plankton samples were collected between 10 am and 1 pm. The density of veligers gradually dropped from 65.5 $L^-$ to 32.5 $L^{-1}$ The veligers were most abundant during the months of July and August, with densities ranging from 5 to 105 $L^-$. FIG. 7 shows that the veliger density dropped well below 10 $L^{-1}$ in early September when the water temperature was still above 20° C. (which is considered an "optimal" temperature for reproduction. The veliger numbers remained low throughout the fall with no second peak as reported by Sprung Arch. Hydrobiol. 115:537-561 (1989). The veligers disappeared from the river waters when the water temperature dropped below 15° C.

Veliger Settlement

During experiments using hydrogen peroxide and chlorine, the number of veligers settling on the PVC plates within the baffled tanks was monitored. The PVC settling plates were subsampled on either the 3rd, 7th or 14th day of the test. Almost no settlement occurred on these plates during any of the tests, even though all of these experiments were carried out when veligers were present in the water at average densities of 28 veligers per liter. This is equivalent to an average of 40,320 veligers/day passing through each baffled tank. It should be noted that by the end of the summer hundreds of small mussels (0.5-3.0 mm) were attached to the inside of each of the constant head tanks.

Chlorine Experiments

Figure 8:
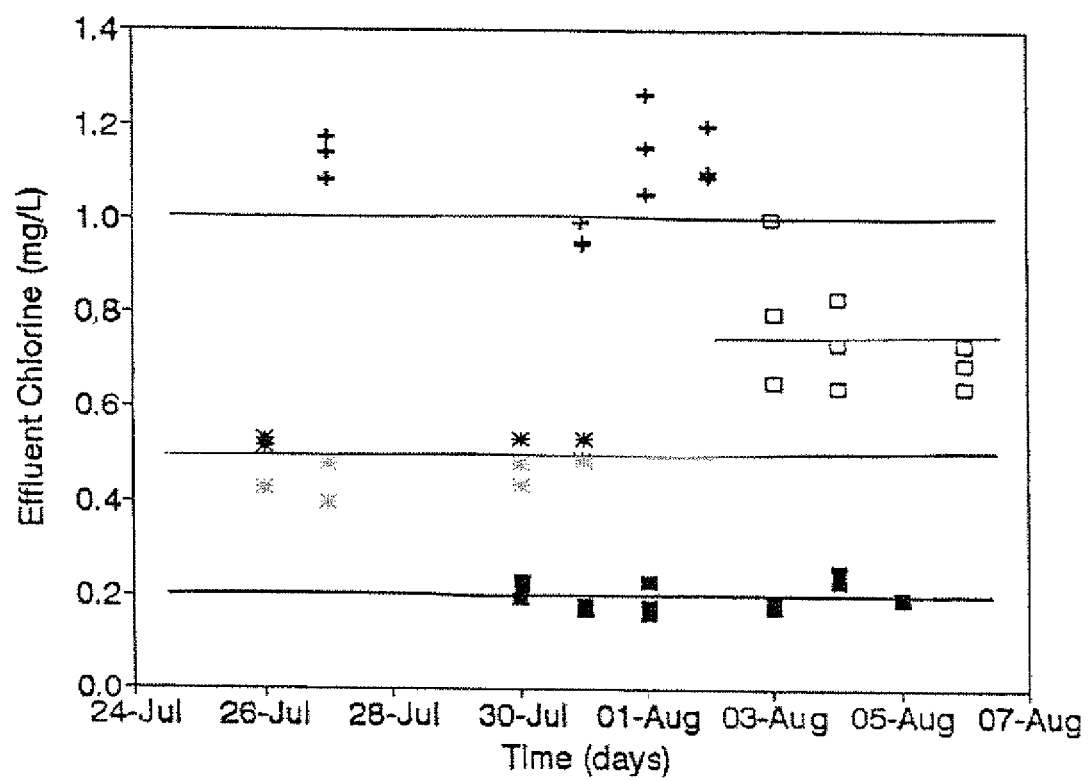
FIG. 8 shows effluent chorine concentrations for the experiments described in Example 2. Solid lines indicate nominal concentration; Symbols are measured data.

Chlorine was added in a continuous mode. Table 2 shows the chlorine residual data within the baffled tanks. Only a small gradient in total chlorine concentration existed in the baffled tanks. FIG. 8 shows the effluent residual data over the course of the four long term chlorine studies. Note the chlorine doses were relatively constant over time and near the nominal values.

TABLE 2

Total Chlorine Residuals Through the Continuous Flow Tanks (all chlorine residuals in mg/L as Cl2)

| Nominal chlorine | Front Baffle | | | Rear Baffle | | | Effluent | | |
| --- | --- | --- | --- | --- | --- | --- | --- | --- | --- |
| | mean | s.d. | n | Mean | s.d. | n | mean | s.d. | n |
| 0.2 | 0.22 | 0.01 | 6 | 0.18 | 0.01 | 6 | 0.20 | 0.03 | 18 |
| 0.5 | 0.58 | 0.04 | 9 | 0.48 | 0.06 | 9 | 0.48 | 0.04 | 12 |
| 1.0 | 1.18 | 0.08 | 9 | 1.02 | 0.12 | 9 | 1.10 | 0.10 | 12 | s.d. = standard deviation, n = number of measurements.

Although no settling was observed in the baffled tanks during the experiments, chlorine did appear to have adverse effects on the veligers. In all the chlorine tests, less than 5% of the veligers that entered the baffled tanks were observed in the tank effluents. Table 3 compares the effluent veliger densities of the tanks receiving chlorine and the control tanks. Due to the variation in densities over time, the percent loss relative to each control is given (% loss=(1−mean veliger density in test tank/mean veliger density in control)×100). The percent loss was over 97% for chlorine concentrations ranging from 0.1 to 1.0 mg/l.

At the termination of the seven day experiments at chlorine residuals of 0.2 and 1.0 mg/l, selected sediment subsamples were examined for veligers. Table 4 shows the estimated number of veligers found per square cm. Almost all of these veligers (in control and treated sediments) were dead. The difference between the controls and treatment tanks is most notable in the first portion of the tanks. The sediment data partially account for the veligers that did not leave in the effluent of the experimental tank. During the 1.0 mg/l chlorine test, the mean veliger density was 47.6 $L^-$. Approximately 479,400 veligers entered each experimental tank with almost none leaving (see Table 3). From the sediment data, approximately 231,800 dead veligers were estimated to be in only the first portion of the experimental tank. Thus almost half (48%) of the missing veligers are accounted for by examining the sediments in the first section of the tank.

TABLE 3

Effluent Veliger Concentrations in the Chlorine Tests
(effluent veliger concentrations in number/L).

| Nominal chlorine | Tanks Receiving Chlorine | | | Control | | | Mean Percent |
|---|---|---|---|---|---|---|---|
| (mg/L) | mean | s.d. | n | mean | s.d. | n | Removed (%) |
| 0.2 | 0.05 | 0.12 | 6 | 20.6 | 0.07 | 2 | 99.8 |
| 0.5 | 1.10 | 1.30 | 6 | 44.6 | 49.4 | 2 | 97.5 |
| 0.75 | 0 | — | 2 | 15.8 | — | 1 | 100 |
| 1.0 | 0.05 | 0.12 | 6 | 37.7 | 32.0 | 2 | 99.9 |
| 0.1 | 0 | — | 1 | 0.7 | — | 1 | 100 |
| 1.0 | 0 | — | 1 | 0.9 | — | 1 | 100 |

TABLE 4

Quantification of Veligers in Sediments After Chlorination
(values of numbers of veligers per cm$^2$)

| Area# | Control | 1 mg/L Cl$_2$ | Control | 0.2 mg/L Cl$_2$ |
|---|---|---|---|---|
| 1 | 109 | 1887 | 94 | 554 |
| 2 | 1.8 | 120 | 63 | 90 |
| 3 | 1.9 | 3.4 | 8.8 | 2.2 |

Chlorination of Juvenile Mussels

Figure 3:
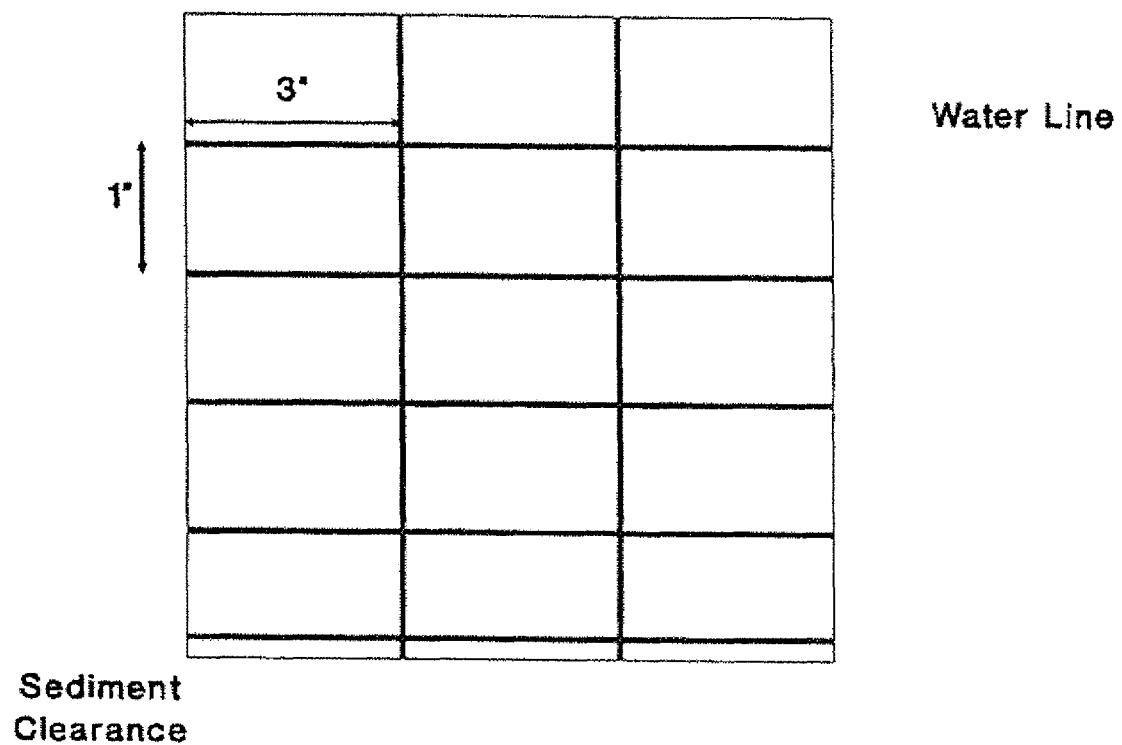
FIG. 3 is a schematic representation of the PVC settling plates used in Example 2.
Figure 9:
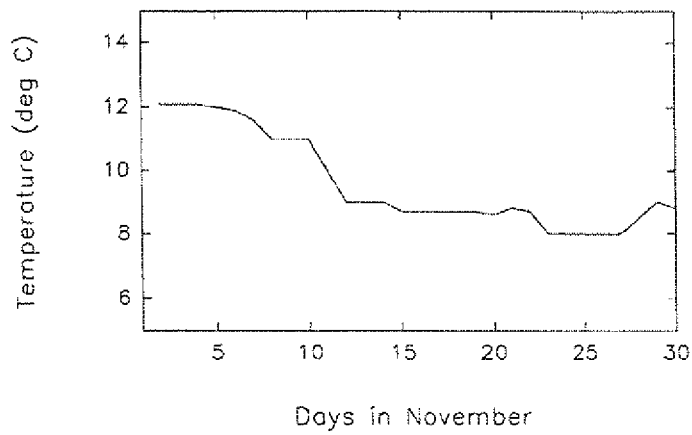
FIG. 9 shows experimental temperature (A), turbidity (B) and chlorine residuals for the month November as described in Example 2.
Figure 9:
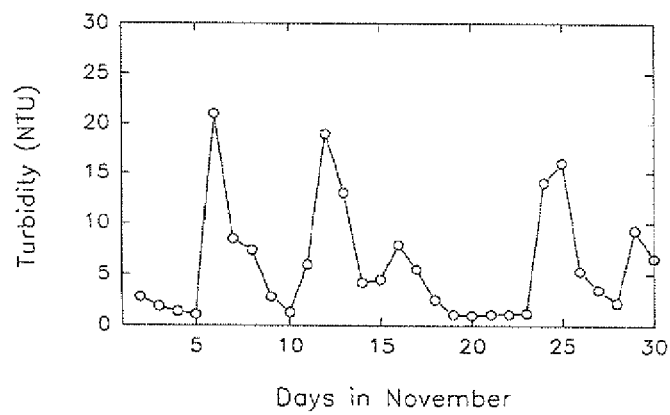
Figure 9:
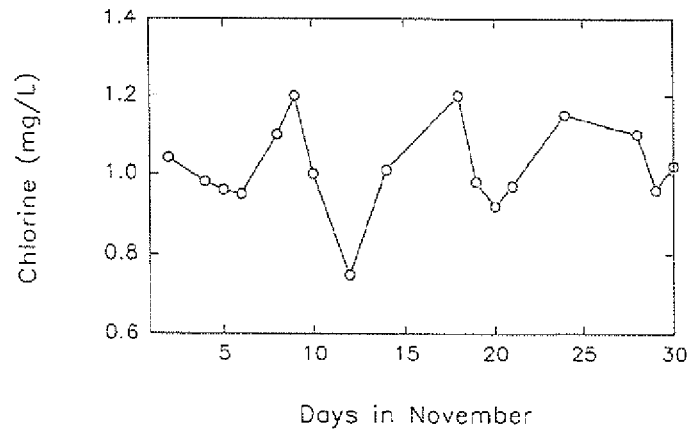

Chlorination of the juvenile mussels occurred in November. During this period, the temperature was initially 12.1° C. and dropped to 8.0° C. (FIG. 9). During the first half of November, there were periods of high turbidity (FIG. 9B). The mussels were exposed continually to a mean total chlorine residual of 1.2 mg/l (std. dev=1.4) (FIGS. 3.8).

Figure 10:
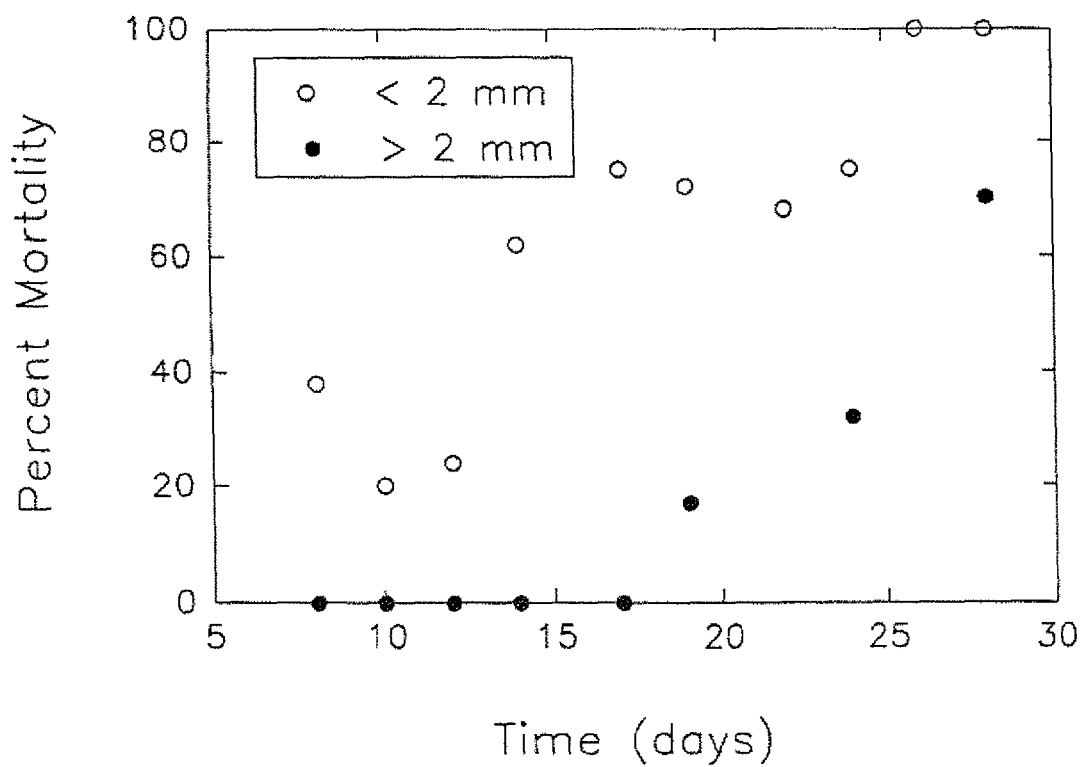
FIG. 10 shows mortality during experiments on the chlorination of juvenile mussels as described in Example 2.

The mussels were divided into two size classes: 0.75-2 mm and 2.5-5 mm. FIG. 10 shows the increase in mortality as a function of time. Sampling of the seeded plates did not begin until the 8th day of exposure. It appears that the smaller mussels experienced mortality before the 8$^{th}$ day. Therefore, the lag period before first mortality in the smaller mussels is unknown. In contrast, all of the larger juveniles survived chlorination through 17 days. For the smaller mussels, 100% mortality was reached on day 26 of exposure. After 28 days of exposure, the larger juveniles exhibited 70% mortality.

It will be appreciated that certain features of the invention, which are, for clarity, described in the context of separate embodiments or separate aspects, may also be provided in combination in a single embodiment. Conversely, various features of the invention, which are, for brevity, described in the context of a single embodiment or aspect, may also be provided separately or in any suitable sub-combination.

Although the invention has been described in conjunction with specific embodiments thereof, if is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present invention.

The invention claimed is:

1. A two-stage method for controlling bivalve growth in a service water system of a plant wherein service water is drawn from a body of water and generally continuously flowed through the service water system, the method comprising:
   a. monitoring the body of water for the presence of veligers and/or early stage bivalves;
   b. subsequent to detecting an increase in the concentration of veligers and/or early stage bivalves, introducing hypochlorite anion into the service water of the service water system in an amount sufficient to obtain a steady state hypochlorite anion concentration of 0.1 to 0.3 mg/l;
   c. maintaining the steady state concentration of hypochlorite anion in the service water of the service water system for a first treatment period of 10 to 40 days;
   d. monitoring the body of water for the presence of pediveligers;
   e. subsequent to detecting an increase in the concentration of pediveligers, introducing hypochlorite anion into the service water of the service water system in an amount sufficient to obtain a steady state hypochlorite anion concentration of 0.4 to 2.0 mg/l;
   f. maintaining the steady state concentration of hypochlorite anion in the service water of the service water system for a second treatment period of 10 to 40 days.

2. The method of claim 1, further comprising monitoring a live colony of the bivalves in the service water of the service water system or under hypochlorite anion concentrations and temperatures comparable to those in the service water system and terminating the second treatment period after the bivalves in the live colony die.

3. The method of claim 1, wherein the first treatment period is initiated in May, June or July and the second treatment period is initiated in August, September, October, November or December.

4. The method of claim 1, wherein the first treatment period is initiated 4 to 6 weeks after the increase in the concentration of veligers and/or early stage bivalves is detected.

5. The method of claim 1, wherein the second treatment period is initiated 8 to 24 weeks after the first treatment period is terminated.

6. The method of claim 1, wherein the hypochlorite anion is introduced in the form of an aqueous solution of a hypochlorite salt.

7. The method of claim 6, wherein the hypochlorite salt is NaOCl.

8. The method of claim 1, wherein the method further comprises analyzing the hypochlorite anion concentration in the service water and increasing or decreasing the amount of hypochlorite anion introduced into the service water in order to maintain the steady state hypochlorite anion concentration.

9. The method of claim 1, wherein the method further comprises neutralizing residual hypochlorite anion in an effluent from the service water system.

10. The method of claim 9, wherein the residual chlorine anion is neutralized with a sulphur based compound.

11. The method of claim 1, further comprising:
   i. seeding a water permeable container with a sample of live bivalves;
   ii. acclimatizing the live bivalves to ambient conditions of the service water;
   iii. placing the container in the service water of the service water system or in water that has hypochlorite anion concentrations and temperatures comparable to those in the service water system; and,
   iv. determining the viability of the bivalves in the container, wherein bivalve mortality is correlated with the effectiveness of the treatment.

12. The method of claim 1, wherein the bivalves are zebra mussels and/or quagga mussels.

13. The method of claim 1, wherein step e. comprises introducing hypochlorite anion into the service water of the service water system in an amount sufficient to obtain a steady state hypochlorite anion concentration of 0.5 to 1.0 mg/l.

14. The method of claim 1, wherein step b. comprises introducing hypochlorite anion into the service water of the service water system in an amount sufficient to obtain a steady state hypochlorite anion concentration of less than 0.2 mg/l.

15. The method of claim 10, wherein the sulphur based compound is sodium bisulphite.

16. The method of claim 1, wherein step (b) comprises introducing hypochlorite anion into the service water of the service water system in an amount sufficient to obtain a steady state hypochlorite anion concentration of less than 0.2 mg/l and step (e) comprises introducing hypochlorite anion into the service water of the service water system in an amount sufficient to obtain a steady state hypochlorite anion concentration of 0.4 to 0.8 mg/l.

* * * * *